(12) United States Patent
Lagunavicius et al.

(10) Patent No.: US 9,102,796 B2
(45) Date of Patent: Aug. 11, 2015

(54) TRANSFECTION REAGENT

(75) Inventors: Arunas Lagunavicius, Vilnius (LT); Sarunas Zigmantas, Vilniaus raj. (LT); Laurynas Riauba, Vilnius (LT); Lolita Zaliauskiene, Vilnius (LT); Richard Makuska, Vilnius (LT); Ausvydas Vareikis, Vilnius (LT); Ula Bernadisiute, Vilnius (LT)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 825 days.

(21) Appl. No.: 12/333,453

(22) Filed: Dec. 12, 2008

(65) Prior Publication Data

US 2010/0041739 A1 Feb. 18, 2010

(30) Foreign Application Priority Data

Dec. 12, 2007 (GB) .................................. 0724253.0

(51) Int. Cl.
| | |
|---|---|
| A61K 47/30 | (2006.01) |
| A61K 48/00 | (2006.01) |
| C08G 73/00 | (2006.01) |
| C12N 5/00 | (2006.01) |
| C08G 73/02 | (2006.01) |
| A61K 47/48 | (2006.01) |
| C08F 251/00 | (2006.01) |
| C08F 283/00 | (2006.01) |
| C08F 290/14 | (2006.01) |
| C12N 15/88 | (2006.01) |

(52) U.S. Cl.
CPC ...... *C08G 73/0206* (2013.01); *A61K 47/48192* (2013.01); *C08F 251/00* (2013.01); *C08F 283/00* (2013.01); *C08F 290/14* (2013.01); *C08F 290/145* (2013.01); *C12N 15/88* (2013.01)

(58) Field of Classification Search
CPC ................... A61K 48/0041; A61K 47/48192; C08F 283/00; C08F 290/14; C08F 290/145; C08G 73/0206
See application file for complete search history.

(56) References Cited

U.S. PATENT DOCUMENTS

| | | | |
|---|---|---|---|
| 5,595,897 A | 1/1997 | Midoux et al. | |
| 6,013,240 A | 1/2000 | Behr et al. | |
| 6,080,724 A | 6/2000 | Chassaing et al. | |
| 6,184,037 B1 | 2/2001 | Rolland et al. | |
| 6,184,038 B1 | 2/2001 | O'Hare et al. | |
| 6,413,941 B1 | 7/2002 | Garnett et al. | |
| 6,433,017 B1 | 8/2002 | Felgner et al. | |
| 6,566,114 B1 | 5/2003 | Kauppinen et al. | |
| 6,770,479 B1 * | 8/2004 | Lee et al. | 435/456 |
| 6,825,341 B2 * | 11/2004 | Leclerc et al. | 536/55.3 |
| 6,841,535 B2 | 1/2005 | Divita et al. | |
| 8,173,131 B2 | 5/2012 | Tripp et al. | |
| 2001/0005717 A1 | 6/2001 | Wagner et al. | |
| 2004/0142474 A1 | 7/2004 | Mahato et al. | |
| 2004/0203154 A1 | 10/2004 | Trubetskoy et al. | |
| 2004/0248842 A1 | 12/2004 | Wagner et al. | |
| 2006/0204444 A1 | 9/2006 | Young et al. | |

FOREIGN PATENT DOCUMENTS

| | | |
|---|---|---|
| EP | 0 285 010 A2 | 10/1988 |
| EP | 0 755 924 A1 | 1/1997 |
| EP | 1 316 318 A2 | 6/2003 |
| EP | 1 316 318 A3 | 12/2003 |
| EP | 2 070 970 A2 | 6/2009 |
| GB | 2 148 266 A | 5/1985 |
| JP | 2006-233290 A | 9/2006 |
| WO | WO 95/24221 A1 | 9/1995 |
| WO | WO 96/02655 A1 | 2/1996 |
| WO | WO 99/36089 A1 | 7/1999 |
| WO | WO 01/43778 A1 | 6/2001 |
| WO | WO 02/42426 A2 | 5/2002 |
| WO | WO 03/087471 A1 | 10/2003 |
| WO | WO 03/095641 A1 | 11/2003 |
| WO | WO 2004/096998 A2 | 11/2004 |
| WO | WO 2005/060934 A1 | 7/2005 |
| WO | WO 2009/142893 A2 | 11/2009 |

OTHER PUBLICATIONS

Zaliauskiene, et al. (2010) "Efficient Gene Transfection Using Novel Cationic Polymers Poly(hydroxyalkylene imines)", Bioconjugate Chemistry, 21(9): 1602-11.*
Li, et al. (May 1, 2006) "Synthesis of lipopolyhydroxyalkyleneamines for gene delivery", Bioorganic & Medicinal Chemistry Letters, 16(9): 2428-32.*
European Search Report dated Mar. 9, 2010 (Two (2) pages), EP08170995.8-2115/2070970, Sep. 3, 2010, Application to Fernentas UAB.
Bragonzi, A. et al., "Comparison between cationic polymers and lipids in mediating systemic gene delivery to the lungs", Gene Therapy, (1999), vol. 6, pp. 1995-2004.
Brown, M. D. et al., "Gene delivery with synthetic (non viral) carriers", International Journal of Pharmaceutics, (2001), vol. 229, pp. 1-21.
De Smedt, S. C. et al., "Cationic Polymer Based Gene Delivery Systems", Pharmaceutical Research, (2000), vol. 17, No. 2, pp. 113-126.
Ferrari, S. et al. "ExGen 500 is an efficient vector for gene delivery to lung epithelial cells in vitro and in vivo", Gene Therapy, (1997), vol. 4, pp. 1100-1106.
Florea, B. I. et al., "Transfection Efficiency and Toxicity of Polyethyleneimine in Differentiated Calu-3 and Nondifferentiated Cos-1 Cell Cultures", The AAPS PharmSci, (2002), vol. 4, No. 3, article 12, pp. 1-11.
Gao, X. et al., "Nonviral Gene Delivery: What We Know and What is Next", The AAPS Journal, (2007), vol. 9, No. 1, article 9, pp. E92-E104.

(Continued)

*Primary Examiner* — Robert M Kelly
(74) *Attorney, Agent, or Firm* — Thompson Hine LLP

(57) ABSTRACT

The present invention relates to a polyalkyleneimine polymer having a repeat unit comprising a hydrophilic group, agents containing the same and methods for their use.

16 Claims, 12 Drawing Sheets

(56) References Cited

OTHER PUBLICATIONS

Gosselin, M. A. et al., "Efficient Gene Transfer Using Reversibly Cross-Linked Low Molecular Weight Polyethylenimine", Bioconjugate Chem., (2001), vol. 12, pp. 989-994.

Forrest, M. L. et al., "A Degradable Polyethylenimine Derivative with Low Toxicity for Highly Efficient Gene Delivery", Bioconjugate Chem., (2003), vol. 14, pp. 934-940.

Patil, S. D. et al., "DNA-based Therapeutics and DNA delivery systems: A Comprehensive Review", The AAPS Journal, (2005), vol. 7, No. 1, article 9, pp. E61-E77.

British Search Report dated Apr. 14, 2008 (Four (4) pages), GB0724253.0, to Fermentas.

Antoine Kichler, "Gene Transfer with modified polyethylenimines", The Journal of Gene Medicine, Review Article, 2004, pp. S3-S10, vol. 6.

Francoise Leclercq et al., "Synthesis of Glycosylated Polyethylenimine with Reduced Toxicity and High Transfecting Efficiency", Bioorganic & Medicinal Chemistry Letters, 2000, pp. 1233-1235, vol. 10.

Protein transfection reagent Saint-PhD. Synvolux Therapeutics. http://www.synvolux.com/protein-transfection-reagent-saint-phd.html. Accessed: Jul. 2, 2011 (one (1) sheet).

DeliverX™ Peptide Transfection Kits. Panomics. http://www.panomics.com/product/43/. Copyright 2009. Accessed: Sep. 29, 2009 (two (2) sheets).

DeliverX™ Peptide Transfection Kit. Panomics. Copyright 2006 (two (2) sheets).

Baranauskas, Aurimas, "Biochemical Properties of methyl-specific restriction endonuclease," Biochemistry Master's Thesis, Vilnius University (2006). Abstract only. (three (3) sheets).

Klimasauskas, Saulius, "New enzymes and technologies epigenetics analysis," Project EPIGEN, Biotechnologijos Institutas, Registration No. P-07003, Contract No. P-03/2008 (2008). Abstract only. (three (3) sheets).

Roberts, Josh, "Buyer's Guide to Protein Transduction Reagents—A range of chemicals and peptides are available to help get proteins into cells," The Scientist (Jun. 7, 2004) vol. 18 Pt. 11, pp. 42 and 43 (two (2) sheets).

Chariot™ Simple, efficient protein delivery,. http://www.activemotif.com/documents/5.pdf. Oct. 12, 2009, (six (6) sheets).

Great Britain Search Report on GB0917792.4, dated Feb. 11, 2010 (four (4) sheets).

"Pep-1 (Uncapped)," Genscript, http://www.genscript.com/peptide/RP10130-Pep-1_peptide.html. Accessed: Sep. 29, 2009 (two (2) sheets).

Futami et al., "Intracellular delivery of proteins into mammalian living cells by polyethylenimine cationization", Journal of Bioscience and Bioengineering, vol. 99, No. 2, pp. 95-103, Feb. 2005 (twelve (12) sheets).

"Voyager™ NES Protein Production Kits," Invitrogen. http://tools.invitrogen.com/content/sfs/manuals/voyagernesprotprodkits_man.pdf. Apr. 7, 2004 (two (2) sheets).

"ProVectin™ Protein Delivery Reagent." Imegenex. http://www.imgenex.com/provectin.php. Accessed: Sep. 18, 2009 (one (1) sheet).

International Search Report and Written Opinion, PCT/EP2010/065236, mailed Mar. 29, 2011 (nine (9) sheets).

"TransVector™," Krackeler Scientific, Inc http://www.krackeler.com/products/fid/2820. Accessed: Sep. 29, 2009 (one (1) sheet).

"Penetratin™ 1 Peptide," Krackeler Scientific, Inc. http://www.krackeler.com/products/fid/2819. Sep. 29, 2009 (two (2) sheets).

"BioPORTER Protein Delivery Reagent," http://www.genlantis.com/objects/catalog/product/extras/1077_Resource_Technical_Updates_No6.pdf. Oct. 12, 2009 (two (2) sheets).

"Pro-Ject Protein transfection reagent," Thermo Scientific. http://www.piercenet.com/Objects/View.cfm?type=productFamily&ID=A21BD675-A083-4D56-A6B0-F1F6BA6DA446. Accessed: Sep. 18, 2009 (two (2) sheets).

"BioTrek TM Protein Delivery Reagent Instruction Manual," Copyright 2003 http://www.stratagene.com/manuals/204140.pdf (seven (7) sheets).

"Profect Protein Delivery Reagents Product Applications Guide 2008," http://www.targetingsystems.net/profect.pdf. Oct. 12, 2009 (six (6) sheets).

"TransPass™ P Protein Transfection Reagent," New England BioLabs Inc. http://www.neb.com/nebecomm/products/productM2563.asp, Accessed: Sep. 29, 2009 (two (2) sheets).

"PULSin™ Delivery Reagent of Functional Proteins/Antibodies and Peptides to Living Cells," http://www.polyplus-transfection.com/EN/produit.php?PAGEID=131. Accessed: Sep. 18, 2009 (three (3) sheets).

"ProteoJuice™ Protein Transfection Reagent," Merck http://www.merckbiosciences.co.uk/Products/ProductDisplay.asp?catno=71281. Sep. 29, 2009 (two (2) sheets).

Harlow, Jay, "Sea Scallops: How to Avoid Getting Soaked," Sally's Place, http://www.sallybernstein.com/food/columns/harlow/sea-scallops.htm (2002) Accessed: Nov. 19, 2012 (three (3) sheets).

Shigeta et al., "Anti-RNA Virus Activity of Polyoxometalates," Biomedicine & Pharmacotherapy, vol. 60, No. 5, pp. 211-219, available online May 24, 2006 (nine (9) sheets).

\* cited by examiner

TRANSFECTION REAGENT

FIELD OF INVENTION

The present invention relates to novel polymers suitable for use as transfection reagents, to agents containing the same, and to methods of their use in delivering macromolecules and compounds comprising at least one nucleic acid to cells.

BACKGROUND OF INVENTION

Current demand for efficient gene delivery agents is huge and still growing. Deciphering of the human genome in 2003 and so-called "postgenomic era" that came afterwards is characterized by large scale research in examining individual genes and corresponding proteins both performed by the academic community and biopharmaceutical industry. These activities require quick access to expressed recombinant proteins. Hence there is high and constant demand for efficient techniques allowing large-scale high throughput production of required proteins after gene transfer.

Lately, the insertion of foreign DNA into bacteria for expression of desired protein has become a routine procedure. This technique is also employed by the pharmaceutical industry both for analysis and production of recombinant proteins with therapeutic potential. The best-known example is synthesis of human insulin in *E. coli* bacteria. However, synthesis of recombinant proteins from higher organisms in bacteria has many limitations. Unlike mammalian (eukaryotic) cells, bacteria lack enzymes and organelles that are responsible for the processing and modification of protein, such as glycosylation, disulfide bond formation, etc. Usually, bacteria cannot fold larger proteins into correct 3D structures that ensure proper biological activity of the protein.

The efficient gene delivery to eukaryotic cells could solve aforementioned problems and could be applied not only for gene delivery, but also in gene therapy. However, transfection of mammalian cells is a much more complicated procedure than the transformation of bacteria.

The ideal gene delivery method in eukaryotic cells should meet three major criteria: (1) it should efficiently bring DNA into the cell's nucleus and release it there, (2) it should protect DNA against degradation by nucleases and other enzymes (3) the method itself should be non-toxic to the host cells.

Viral vectors are effective gene carriers and meet the first two criteria. However, they have some major disadvantages. Usually viruses have to be chemically or physically inactivated in order to eliminate their pathogenic properties. Therefore, the chances of reversion to a pathogenic virus exist, which are often difficult to evaluate. Use of viruses in vivo presents the problem of immunogenicity for animals and humans. Moreover, viral systems are expensive, difficult to use and complicated to handle. In comparison to the other gene carriers, the use of viral vectors requires special equipment in order to ensure safety of applicant and environment. Moreover, the virus envelope has a definitive volume and therefore can deliver limited size DNA.

Nonviral gene delivery systems can overcome most of the obstacles associated with viral vectors. The biggest advantage of nonviral transfection reagents is lower immune response and easier application procedure. Most nonviral gene delivery systems are synthetic materials and can be classified into two major groups: cationic lipids and cationic polymers. In both cases amino groups provide the required positive charge for DNA compactization. Amino groups are also found in naturally occurring transfection agents such as spermine and spermidine. The advantage of amino groups is the ability to abstract protons and gain a positive charge at physiological pH.

Cationic lipids are well-studied DNA carriers. Nonetheless, with the success of polyethyleneimine (PEI) as a transfection reagent, a lot of attention is given to the cationic polymers. Cationic polymers are able to condense DNA into small particles and initiate cellular uptake via endocytosis. However, the transfection activity and toxicity of these polymers varies widely. Cationic polymers can be classified into four major groups:
1) polylysine and its derivatives,
2) chitosan and other sugars possessing amino groups,
3) polyamidoamine dendrimers,
4) polyethyleneimine and its modifications.

Polylysine

Polylysine (PLL) is one of the first cationic polymers that was used as a transfection reagent. Due to it's polypeptide structure, PLL has a biodegradable nature and this property is essential for it's use in vivo. However, PLL exhibits moderate to high toxicity as well as immunogenicity due to it's peptide backbone. Further, its transfection efficiency is relatively low. In addition, PLL complexes with DNA undergo nonspecific binding to cell membrane only in certain cell lines thereby limiting it's use. The pKa value of lysine $\epsilon$-amino group is about 10 and therefore at physiological pH all these amines are protonated. Positively charged PLL can make DNA compact and efficiently transfer it into the cell. However, the PLL-DNA complex cannot rapidly escape from the endosomes, since PLL amino groups are fully protonated and they do not work as a "proton sponge" and cannot facilitate endosmolysis. PLL transfection efficiency can be improved by using it with endosmolytic agents, such as chloroquine. PLL has been used as a graft copolymer with poly(lactic-co-glycolic) acid (PLGA) that serves as endosmolytic agent. The PLL-PLGA graft copolymer demonstrated high transfection efficiency and low toxicity when compared with PLL alone.

The modification of PLL by conjugating histidine to lysine residues resulted in a polymer with higher transfection efficiency than PLL/chloroquine mixture. The pKa value of imidazole group in histidine is around 6, thus it possesses buffering ability, can abstract protons and facilitate polymer-DNA endosomal escape. Furthermore, this polymer is less toxic than PLL alone because of the optimized charge density. Another promising method for preparing PLL based polymers involves replacement of lysine with amino acid cysteine. It was demonstrated that polymers with cross-linked cysteine residues have higher transfection activity, indicating that DNA release is triggered by reduction of disulfide bonds.

The application of PLL as a transfection agent is known, for example from Midoux et al. U.S. Pat. No. 5,595,897 and Yu et al. WO 02/42426. Further, Pharmaceutical Research, Vol. 17, No. 2, 2000 discloses various derivatives of PLL including a PEG-PLL block copolymer, PLL grafted copolymers and PLL with an attached hydrophilic segment like PEG. Cationic copolymers bearing hydrophilic segments also are mentioned.

International Journal of Pharmaceutics 229 (2001) 1-21 "Gene delivery with synthetic (non viral) carriers" discloses covalent attachment of hydrophilic methoxy polyethylene glycol groups to PLL.

Chitosan

Chitosan is a natural biodegradable polymer that shows very low toxicity in the cells. Chitosan size can vary from 1.2 kDa to 500 kDa and as transfection agent it is the most efficient in the molecular range between 30 and 170 kDa. Chitosan forms positively charged toroidal complexes with DNA that protects DNA against DNase degradation. It was shown that more than 65% of chitosan amino groups should be protonated in order to obtain stable complexes able to attach to the cells in vitro. The overall transfection ability of chitosan is relatively low. Like PLL, chitosan has poor buffering capacity and its endosomal escape is also slow. The transfection efficiency of chitosan can be amplified by adding endosmolytic enzyme. The application of chitosan as a gene delivery agent is known, for example from Rolland et al. U.S. Pat. No. 6,184,037.

Polyamidoamine Dendrimers

Polyamidoamine (PAMAM) dendrimers have a 3D spherical structure and they represent a novel class of cationic polymers that are used as transfection agents. The synthesis of dendrimers can be controlled and the degree of branching is expressed in the generation of the dendrimer. Therefore, the PAMAM dendrimers can be produced with low degree of polydispersity and that is a big advantage over other cationic polymers that generate highly polydisperse particles. The uniform size of PAMAM polymers can offer reproducible gene delivery results and potential for clinical application. Dendrimers have a star-like structure with the primary amines on the surfaces and tertiary amines inside. Primary amines are highly charged and they bind DNA, while tertiary amines can abstract protons in the endosomal compartment that results in swelling of the endosome and release of the DNA into the cytoplasm. The hydrolytic degradation of the PAMAM dendrimers yields fractured structures. It has been shown that fractured dendrimers demonstrate strongly enhanced gene expression over corresponding intact polymer. It is thought that fractured polymers have increased flexibility, which is crucial to the swelling of the endosome. QIAGEN offers two commercial sixth generation PAMAM dendrimers as transfection agents: PolyFect, an intact dendrimer, and SuperFect, a fractured dendrimer. The application of dendrimers for gene delivery is known also from Garnet et al. U.S. Pat. No. 6,413,941 and Tomalia et al. WO9524221.

Polyethyleneimine

Polyethyleneimine (PEI) is the most active and most intensively studied cationic polymer to date. Behr's group was the first to show that PEI can be an effective transfection agent U.S. Pat. No. 6,013,240, WO96/02655. PEI can be obtained in branched or linear forms. Branched PEI is known, for example, from AAPS PharmSci 2002; 4(3) article 12 "Transfection Efficiency and Toxicity of Polyethyleneimine in Differentiated Calu-3 and Nondifferentiated Cos-1 Cell Cultures".

Since every third atom in the PEI chain is nitrogen with pKa value 5.5, PEI is very densely charged polymer. At physiological pH one sixth of nitrogen atoms are protonated. Branched PEI has a ratio of primary:secondary:tertiary amine groups approximately 1:1:1.

Both linear and branched PEI can be used for transfection in vitro and in vivo. However, it has been reported that linear PEI is a less toxic, more efficient and faster acting transfection agent than branched PEI. This could be attributed to the phenomenon that linear PEI-DNA complexes are less condensed and they can penetrate the cell wall and subsequently the cell nucleus more efficiently than branched PEI and DNA complexes.

PEI is slightly toxic to the cells and this can be explained by its nonbiodegradable nature. Studies have shown that PEI transfection efficiency is dependent on its molecular weight. The most active are: 25 kDa branched PEI and 22 kDa linear PEI. Longer linear PEI also show similar transfection activity, but they are more toxic. On the contrary, shorter linear PEI is less toxic and less efficient.

It is believed that highly cationic PEI condenses DNA molecules into small particles and facilitates cellular uptake via endocytosis by interacting with negatively charged cell surface sites. Furthermore, PEI has a big buffering capacity and it can act as "a proton sponge" and can ensure endosomal escape.

Several different strategies have been examined in order to increase transfection activity of PEI. AAPS Journal 2007; 9(1) article 9 "Nonviral Gene Delivery: What We Know and What is Next" discloses coupling of low molecular weight PEI with bifunctional cross-linking reagents bearing biodegradable bonds such as disulfide or ester. This resulted in polymers that are as efficient transfection reagents as 25 kDa PEI, but less toxic to the cells. The purpose of the cross-linking relates to the biodegradability of the polymer, since disulfide and ester bonds can be cleaved within the cells. "Efficient gene transfer using reversibly cross-linked low molecular weight polyethylenimine" Bioconjug Chem. 2001; 12: 989-994 discloses PEI crosslinked with dithiobis (succininimidylpropionate) (DSP) or dimethyl.3,3'-dithiobispropionimidate.2HCl (DTBP). "A degradable polyethylenimine derivative with low toxicity for highly efficient gene delivery" Bioconjug Chem. 2003, 14, 934-940 discloses PEI with small diacrylate cross-linkers.

Linear PEI is a commercialized transfection reagent, known in the market as jetPEI and Exgen500.

The linear PEI is used extensively in vivo. It has been used for gene delivery directly to various anatomical sites of experimental animals as well as introduced systemically by intravenous injection. Experiments have shown that linear PEI polyplexes with DNA are superior to cationic liposomes for gene delivery by intravenous and intratracheal administration. (Bragonzi, A., Boletta, A., Biffi, A., Muggia, A., Sersale, G., Cheng, S. H., Bordignon, C., Assael, B. M., Conese, M., 1999. Comparison between cationic polymers and lipids inmediating systemic gene delivery to the lungs. Gene Ther. 6, 1995-2004; Ferrari, S., Moro, E., Pettenazzo, A., Behr, J. P., Zacchello, F., Scarpa, M., 1997. ExGen 500 is an efficient vector for gene delivery to lung epithelial cells in vitro and in vivo. Gene Ther. 4, 1100-1106.)

PEI with PEG graft copolymer is known from AAPS Journal 2005; 7(1) article 9 "DNA-based Therapeutics and DNA delivery systems: A Comprehensive Review. The PEG is a different polymer to the PEI polymer.

In view of the above it will be seen that there is a need to provide further, preferably improved, transfection reagents for delivering DNA into cells.

DESCRIPTION OF INVENTION

As such, a first aspect of the present invention provides a cationic polyalkyleneimine polymer having a repeat unit comprising a hydrophilic group.

Such a polymer having this repeat unit is not previously known and may have advantages over prior art polymers.

It has been found by the present inventors that polymers according to the invention can have improved solubility characteristics and also, surprisingly, improved ability to transfect as compared with the prior art. In particular, the present inventors have found that polymers according to the invention can have superior transfection abilities as compared with commercially available PEI.

The hydrophilic group that is comprised in a repeat unit of the cationic polyalkyleneimine polymer according to the invention is distinguished from a cross-linker, which links first and second polymer chains to form a cross-linked polymer, and a grafted polymer, which is a second, different polymer that is grafted to a first polymer. Neither a crosslinker nor a grafted polymer is comprised in a repeat unit of the first polymer.

In one embodiment, the hydrophilic group is in the polymer backbone.

In one embodiment, the hydrophilic group is pendant from the polymer backbone.

In one embodiment, preferably, there are as many imine groups as hydrophilic groups. (i.e. a 1:1 ratio). In another embodiment, preferably the ratio of imine groups:hydrophilic groups is 2:1.

Typically, the hydrophilic group, referred to elsewhere herein as X1 or X2, comprises a heteroatom.

The cationic polyalkyleneimine polymer according to the invention may be linear or branched. According to the present invention, the term "branched" means branching of the polyalkyleneimine polymer per se. "Branched polyalkyleneimine polymer" does not mean a polyalkyleneimine polymer having a second, different polymer grafted thereto.

Preferably, in the polymer having a repeat unit comprising a hydrophilic group, said repeat unit has a structure as shown in formula V, more preferably formula I:

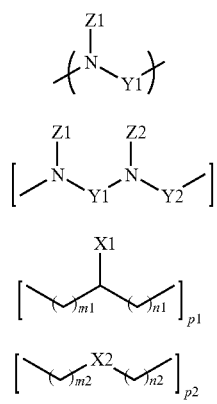

where:
Y1 and Y2 each independently represent a group having formula II or III;
Z1 and Z2 each independently represent —H, alkyl or a branching chain;
X1 represents —H, -alkyl, or a hydrophilic group, X2 represents —CH$_2$—, —CH(alkyl), —C(alkyl)$_2$- or hydrophilic group, provided that at least one of X1 and X2 is a hydrophilic group;
m1, m2, n1 and n2 each independently is 0, 1, 2 or 3; and
p1 and p2 each independently is 1 or 2.

When Z1 and/or Z2 are branching chains it will be understood that Z1 and/or Z2 each represent another cationic alkyleneimine polymer chain having a repeat unit comprising a hydrophilic group. In this way, the cationic alkyleneimine polymer will be branched.

Preferred alkyl Z1 and Z2 groups include —CH$_3$, and —C$_2$H$_5$.

Other repeat units may be present in the polymer.

When Z1=Z2 and Y1=Y2, the cationic alkyleneimine polymer can be a homopolymer of a repeat unit having a structure as shown in formula IV:

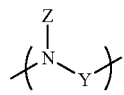

where Z=Z1=Z2 and Y=Y1=Y2. The polymer could be further defined as a homopolymer of AA (formula VII) type or BB (formula VIII) type.

When Z1≠Z2 and/or Y1≠Y2, the cationic alkyleneimine polymer can be a copolymer of a first repeat unit having a structure as shown in formula V and a second, different repeat unit having a structure as shown in formula VI:

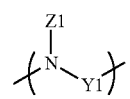

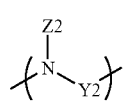

Such polymers could be defined as a copolymer of AA* (formula IX) and BB* (formula X) types. The cationic alkyleneimine polymer may be a regular alternating AB copolymer (formula XI), though a random AB copolymer may be considered also in one embodiment.

Preferred cationic alkyleneimine polymers according to the invention have a repeat unit selected from one of formulae VII to XI:

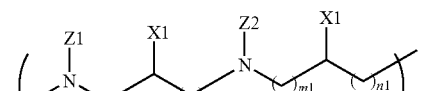

AA homopolymer where Z1=Z2 and, with reference to general formula I, Y1=Y2=a group having formula II.

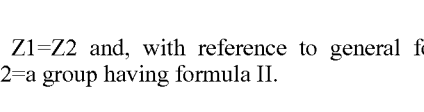

BB homopolymer where Z1=Z2 and, with reference to general formula I, Y1=Y2=a group having formula III.

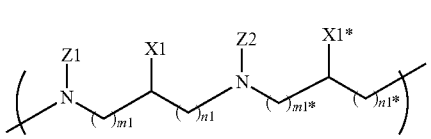

AA* copolymer where Z1 is the same as or different from Z2. In other words, with reference to general formula I, Y1≠Y2 and Y1 and Y2 each independently represent a group having general formula II.

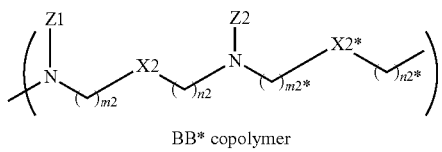

BB* copolymer where Z1 is the same as or different from Z2. In other words, with reference to general formula I, Y1≠Y2 and Y1 and Y2 each independently represent a group having general formula III.

XI

AB copolymer where Z1 is the same as or different from Z2. In other words, with reference to general formula I, Y1≠Y2 and Y1 represents a group having formula II and Y2 represents a group having formula III.

Throughout this specification, the use of "*" means that X1* can be different from X1, X2* can be different from X2, m1* can be different from m1, n1* can be different from n1, m2* can be different from m2, and n2* can be different from n2.

X1 and X1* independently are selected from —H, alkyl, or a hydrophilic group, provided that in formula IX at least one of X1 and X1* represents a hydrophilic group.

Preferably, X1 and X1* independently are selected from the group consisting of —H, alkyl, —OH, —SH, —NH$_2$, —N(alkyl)$_2$, —NH(alkyl), —CONH$_2$, —NHCONH$_2$, —CN

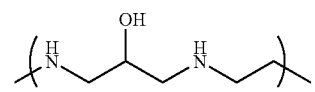

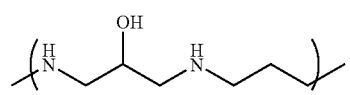

provided that in formula IX at least one of X1 and X1* represents a hydrophilic group (i.e. not H or alkyl in the list above.

X2 and X2* independently are selected from the group consisting of —CH$_2$—, —CH(alkyl)-, C(alkyl)$_2$- and a hydrophilic group provided that in formula X at least one of X2 and X2* represents a hydrophilic group.

Preferably, X2 and X2* independently are selected from the group consisting of —CH$_2$—, —O—, —S—, —NH—, —N(alkyl)-, provided that in formula X at least one of X2 and X2* represents a hydrophilic group (i.e. not —CH$_2$— in the list above).

A preferred polymer according to the invention is poly(2-hydroxypropyleneimine) (pHP), i.e. a homopolymer having an AA a repeat unit of formula XII:

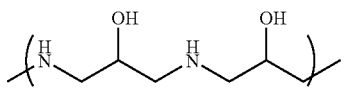

Other preferred polymers according to the invention include poly(2-hydroxypropyleneimine ethyleneimine) (pHPE) and poly (2-hydroxypropyleneimine propyleneimine) (pHPP), i.e. AB copolymers having an AB repeating unit of formula XIII or XIV:

XIII

XIV

The degree of polymerisation (d) of polymers having a repeat unit as shown in any one of general formulae I, or VII to XIV preferably is >1, more preferably in the range from 1 to 1000, more preferably from 30 to 500. Accordingly, a polymer according to the invention may have the formula:

$$-\!\!-\!\!(\text{repeat unit of general formula I})_{\overline{d}}\!\!-\!\!-$$

The molecular weight of the cationic polyalkyleneimine polymer according to the first aspect preferably is in the range of from 1 to 100 kDa, more preferably 5 to 30 kDa. Molecular weight can be measured by size exclusion chromatography (SEC). For a linear polymer, the molecular weight will provide a direct indication of chain length i.e. the degree of polymerisation. However, SEC provides scarce information on polymer branching.

A cationic polyalkyleneimine polymer of the invention may be obtained by any suitable method.

A second aspect of the present invention provides a method of making a cationic polyalkyleneimine polymer as defined in relation to the first aspect by a polycondensation reaction.

A preferred polycondensation reaction is between first monomers each having two reactive groups and second monomers each having two reactive groups, said reactive groups being selected from —Cl, —Br and —I, tosyl, mesyl —NH$_2$ and NHR. A preferred polycondensation reaction is between first monomers each having two reactive groups selected from —NH$_2$ or NH (alkyl) and second monomers each having two halide reactive groups, selected from —Cl, —Br, —I, tosyl and mesyl.

A -tosyl or mesyl group may be used in place of a halide reactive group.

Random copolymers can be obtained by using more than two different monomers in the polymer feed. For example, using three monomers Hal-A-Hal, NH$_2$-A-NH$_2$, and NH$_2$—B—NH$_2$ in the polymer feed for the polycondensation reaction will produce random AB type copolymers. Higher order polymers two also may be made. For example, using 3 monomers Hal-A-Hal, NH$_2$—B—NH$_2$, Hal-C-Hal in the polymer feed for the polycondensation reaction will produce random ABC type copolymers.

It will be appreciated that repeat units as illustrated throughout this application may be derived from a single monomer carrying suitable reactive groups. Similarly, repeat units as illustrated throughout this application may be derived from two or more monomers, each carrying suitable reactive groups.

The two reactive groups on a single monomer could be the same or different from one another. However, for ease of processing they will generally be the same.

In one embodiment, the halide reactive groups are both Br.

In one embodiment, the first monomer has formula XV:

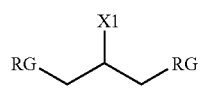

where RG represents a reactive group as defined anywhere herein and X1 represent a hydrophilic group as described anywhere herein.

Preferably, X1 represents OH.

A single monomer may have only two or more than two reactive groups selected from the reactive groups defined above.

Preferably, the ratio of first monomer:second monomer in the polymer feed is in the range 52:48 to 48:52, more preferably about 50:50.

The molecular weight distribution of the cationic polyalkyleneimine polymer produced according to the method of the second aspect preferably is in the range of from 1 to 100 kDa, more preferably 5 to 30 kDa. Molecular weight distribution can be measured by size exclusion chromatography.

One general reaction scheme for a polycondensation reaction is shown below:

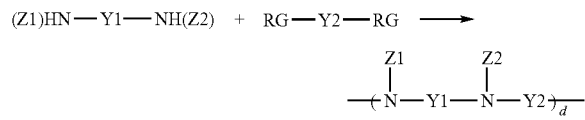

where d is the degree of polymerisation; RG represents a reactive group selected from —Cl, Br, —I, -tosyl and -mesyl; and Z1, Y1 and Y2 are as defined anywhere herein.

The product of the method according to the second aspect may be linear polymers, branched polymers or a mixture of linear and branched polymers.

During the polycondensation reaction, some branching may occur. Branching occurs by the replacement of H by another covalently bonded chain of that polymer.

Suitable solvents in which to carry out the polycondensation reaction will be known to a person skilled in this art and include methanol or a mixture of methanol and water.

A suitable temperature at which to carry out the polycondensation reaction will be known to a person skilled in this art. A suggested temperature is about 10° C. lower than the reflux temperature of the reaction mixture, preferably about 50° C.

The polymer product of the polycondensation reaction may be purified by one or more suitable purification techniques, for example by visking dialysis, as is known in the art.

The purified polymer product may be concentrated by one or more suitable techniques, for example by freeze drying, as is known in the art.

A third aspect of the present invention provides the use of a cationic polyalkyleneimine polymer as defined in relation to the first aspect as a transfection reagent.

A fourth aspect of the present invention provides a composition comprising a cationic polyalkyleneimine polymer as defined in relation to the first aspect and at least one nucleic acid. The at least one nucleic acid may be a deoxyribonucleic acid or a ribonucleic acid. More preferably, said at least one nucleic acid is DNA.

A fifth aspect of the present invention provides a composition comprising a polyalkeneimine polymer as defined in relation to the first aspect and a macromolecule. The macromolecule preferably is an anionic polymer. Preferred anionic polymers include DNA and RNA.

The at least one nucleic acid or macromolecule may be of natural or artificial origin.

In the composition, the cationic polyalkyleneimine polymer condenses the at least one nucleic acid or macromolecule into a small particle. A complex may be formed between the cationic polyalkyleneimine polymer and the at least one nucleic acid or macromolecule, also called a polyplex.

The composition according to the fourth or fifth aspect may contain one or more adjuvants, as is known in the art. This is to improve the transfer of the at least one nucleic acid or macromolecule to the cell, when said composition is used in a method according to the seventh aspect. The one or more adjuvants may comprise a lipid, protein, lipopolyamine, or synthetic polymer.

A sixth aspect of the present invention provides an agent suitable for delivering at least one nucleic acid or macromolecule to a cell, said agent comprising a composition as defined in relation to the fourth or fifth aspect.

Preferably, the cell is a eucaryotic cell.

Preferably the diameter size of the complex is in the range of from 50 nm to 150 nm, more preferably 70 to 100 nm.

The agent may contain a pharmaceutically acceptable vehicle, for example a pharmaceutically acceptable vehicle suitable for an agent to be intravenously injected.

A seventh aspect of the present invention provides a method of delivering at least one nucleic acid or a macromolecule to a cell comprising a step of contacting an agent as defined in relation to the sixth aspect with the cell. The method may be carried out in vitro or in vivo i.e. the cell may be isolated from or may be contained in a live human or animal body. When the method is carried in vitro, the cell may be comprised in a cultured cell line.

The at least one nucleic acid or a macromolecule preferably has a function such that it has a therapeutic effect on the cell when it is delivered thereto. In this respect, the method according to the seventh aspect may be comprised in a method for the treatment of a disorder.

When the method is carried out in vivo, the agent may be introduced into the human or animal body via any suitable technique, for example by intravenous injection or by application to the skin or the mucosae.

When the method is carried out in vitro, the cell may be administered to the agent or vice versa.

An eighth aspect of the present invention provides a method of making a composition as defined in relation to the fourth or fifth aspect or an agent as defined in relation to the sixth aspect. The method comprises the steps of:

1. providing a solution containing the at least one nucleic acid or macromolecule;
2. mixing the solution with a cationic polyalkyleneimine polymer as defined in relation to the first aspect to form a polyplex.

The present invention now will be described in more detail with reference to the attached figures, in which.

EXAMPLES

Figure 1:
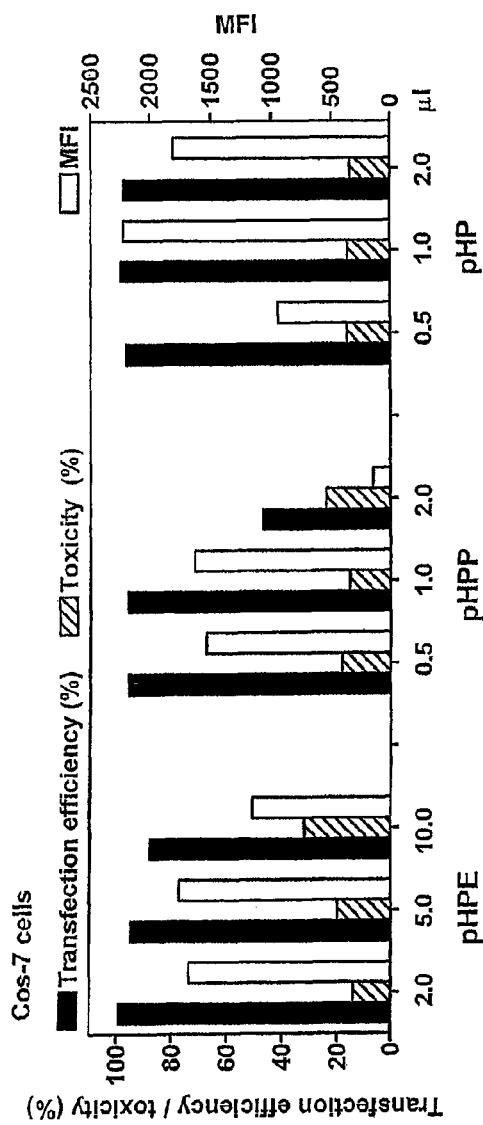
FIG. 1 shows transfection efficiency of PHPE, pHPP and pHP using Cos-7 cells.

Preparation of Polymers According to the Invention

Three polymers according to the invention possessing hydroxy groups have been synthesized. These are:
1. poly(2-hydroxypropyleneimine) (pHP)
2. poly(2-hydroxypropyleneimine ethyleneimine) (pHPE); and
3. poly(2-hydroxypropyleneimine propyleneimine) (pHPP)

These hydroxyalkyleneimine polymers were obtained using polycondensation reactions as shown below:

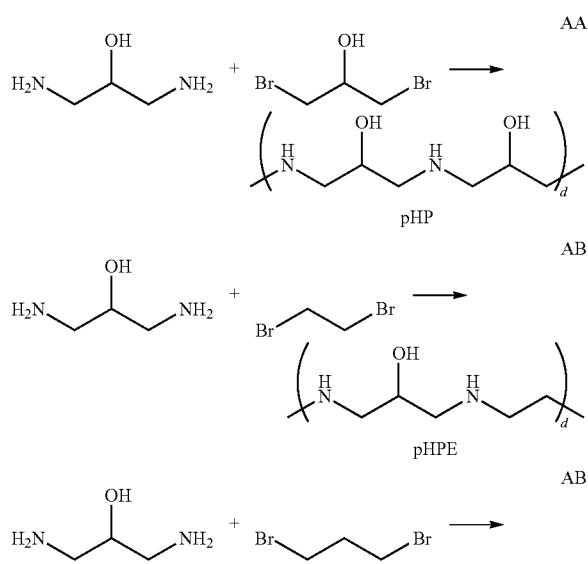

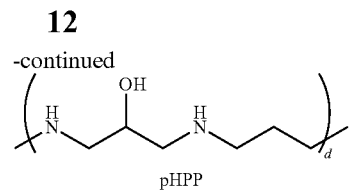

The polycondensation reaction is a stepwise process. Therefore, in order to obtain polymers with higher molecular weight, equal monomer molar ratios were used in the synthesis. The reaction was carried out in methanol at 50° C. for 24-48 hours. Polymers were purified by visking dialysis (cut-off 4 kDa) and concentrated by freeze-drying. The yields of the polymers varied from 21% to 32%.

Synthesis of pHP

In a three-neck 50 mL round-bottom reaction flask, fitted with a stirrer, dropping funnel and a thermometer, 1,3-di-amino-2-propanol (1.5 g) was dissolved in methanol (3 mL). Resulting solution was preheated 50° C. and upon vigorous stirring 1,3-dibromo-2-propanol (3.63 g, 1.7 mL) was added. Reaction mixture was stirred for 48 hours at 50° C. Upon completion the viscous polycondensation reaction mixture was diluted with distilled water (10 mL) and dialyzed against water for 5 days with SERVA Membra-Cel visking dialysis tubing MWCO 4 kDa. Dialysis solution was concentrated under reduced pressure until ca 25% of starting volume and then freeze-dried to furnish pHP poly(2-hydroxypropylene imine) (0.78 g, 32%).

Synthesis of pHPE

To the stirred solution of 1,3-diamino-2-propanol (3.00 g) in methanol (4 mL) in a three-neck 50 mL round-bottom reaction flask, equipped with a stirrer, dropping funnel and a thermometer, 1,2-dibromoethane (6.25 g, 2.87 mL) was added drop-wise. The resulting solution was stirred for 48 hours at 50° C. Resulting viscous polycondensation reaction mixture was diluted with distilled water (10 mL) and dialyzed against water for 5 days with SERVA Membra-Cel dialysis tubing MWCO 4 kDa. Dialysis solution was concentrated under reduced pressure and resulting polymer was further dried using oil pump to give pHPE (poly(2-hydroxypropy-lene imine ethyleneimine) (0.81 g, 21%).

Synthesis of pHPP

To the stirred preheated (50° C.) solution of 1,3-diamino-2-propanol (3.00 g) in methanol (4 mL) in a three-neck 50 mL round-bottom flask, equipped with a stirrer, dropping funnel and a thermometer 1,3-dibromopropane (6.72 g, 3.38 mL) was added drop-wise. Resulting solution was stirred for 24 hours at 50° C. Upon completion the viscous polycondensation reaction mixture was diluted with distilled water (10 mL) and dialyzed against water for 5 days with SERVA Membra-Cel visking dialysis tubing MWCO 4 kDa. Dialysis solution was concentrated under reduced pressure until ca 25% of starting volume and then freeze-dried to yield pHPP (poly(2-hydroxypropylene imine propylene imine) (1.2 g, 28%).

Analysis of Polymers

The structure of the novel polymers was confirmed by FTIR, $^1$H NMR and XPS spectroscopy. FTIR absorption bands in the regions 2837-2855, 2061-2064 and 1624-1637 $cm^{-1}$ are specific for protonized imine groups $NH^+_2$. The absorption band in the region at 3400-3415 $cm^{-1}$ evidences the presence of $NH^+_2$ and OH groups. Strong absorption band at 1070-1108 cm$^{-1}$ is consistent with hydroxyl groups. The signals of $^1$H NMR spectra in D$_2$O at 2.7-3.2 ppm were assigned to C$\underline{H}_2$—NH, while the signal at 4.0-4.2 ppm was evidencing the presence of C$\underline{H}$—OH.

The assignment of different nitrogen groups in XPS spectra under the N 1 s peak was as follows: imine NH ((398.2-398.5 eV), amine NH$_2$ (399.7-399.8 eV) and protonized imine NH$^+$ or amine NH$_2^+$ (401.0-402.5 eV). Deprotonization of pHPE (poly(ethylene imine 2-hydroxypropylene imine)) resulted in disappearance of the peak at 401-402 eV.

Polymers pHPE, pHPP and pHP were additionally characterized by using size exclusion chromatography (SEC) with triple detection, light scattering, viscometer and refractive index (Table 1). Weight average molecular weights of poly-hydroxyalkylimine polymers are in the range from 8,000 Da for pHPE to 20,000 Da for pHPP with polydispersity indexes (Mw/Mn) correspondingly ranging from 1.67 to 2.98. The polyhydroxyalkylimine polymers hydrodynamic radius is 2-3 nm and intrinsic viscosity varies from 0.088 for PHPE to 0.128 for pHPP.

Table 1 below shows quantitative results of poly-hydroxyalkylimine polymers: Weight-average molecular weight (Mw), Number average molecular weight (Mn), Intrinsic viscosity (IV), and Hydrodynamic Radius (Rh).

| Polymer | Mw (kDa) | Mn (kDa) | Mw/Mn | IV (dl/g) | Rh (nm) |
|---|---|---|---|---|---|
| pHPE | 7,868 | 4,705 | 1.67 | 0.088 | 2.11 |
| pHP | 14,473 | 5,832 | 2.48 | 0.126 | 2.78 |
| pHPP | 20,091 | 6,768 | 2.98 | 0.128 | 3.10 |

Essentially, polymers pHPE, pHPP and pHP are soluble in water at physiological pH. This is a very important distinguishing feature since cationic polyalkyleneimine polymer PEI is soluble in aqueous solutions only at pH 4. Thus, it can be postulated that the protonization of imine groups of poly-alkyleneimine polymers at pH 7 is not sufficient to transfer polymers into aqueous solutions. Introduction of hydrophilic groups like hydroxy in the polymer chain increases polymer solubility and it is perfectly soluble at physiological pH.

Considering the fact that PEI polymer precipitates at physiological pH, the appropriate mixing conditions should be applied to form polyplexes with DNA. Solubility is not a problem using pHP and other hydroxyalkyleneimine polymers. Therefore the preparation of polyhydroxyalkyleneimine complexes with DNA is easier than using PEI.

One of the major characteristics of cationic polymers is N/P ratio, the amount of the polymer nitrogens required for neutralization of one DNA phosphate group (Table 2).

Table 2 below shows a comparison of N/P ratios of polyhydroxyalkyleneimines and ExGen500 required for transfection of Cos-7 cells.

| Polymer | Optimal volume, μl* | N/P ratio |
|---|---|---|
| pHPE | 5.0 | 143.7 |
| pHPP | 1.0 | 25.6 |
| pHP | 1.0 | 22.8 |
| ExGen500 | 3.2 | 5.8 |

*Optimal volume of 0.5% solution in water of pHPE, pHPP and pHP and 5.47 mM in terms of nitrogen residues solution in water of ExGen500.

As shown in Table 2, N/P ratios of polyhydroxyalkyleneimines are more than 1, and this indicates that polyhydroxyalkyleneimines with DNA form polyplexes that are positively charged. As it was discussed, other cationic polymers also form positively charged polyplexes and enter the cell via endocytosis by interacting with negatively charged cell surface sites. Arguably, polyhydroxyalkyleneimines enter the cell using the same pathway as other cationic polymers.

The polyhydroxyalkyleneimines form polyplexes with DNA N/P at a higher ratio than ExGen500. The reason for this evidence is not clear, but most importantly higher amount of hydroxyalkyleneimine polymers in the polyplex has no effect on toxicity and transfection efficiency of these reagents.

Transfection Efficiency of Hydroxyalkyleneimine Polymers

The most important requirement for gene carriers is the ability to condense DNA into small particles, called polyplexes. It is shown here that by mixing hydroxyalkyleneimine polymers with DNA in 0.15 M NaCl solution, they form polyplexes with particle size 50-150 nm. This is a suitable size of cationic polymer polyplex with DNA that can be efficiently transfected into the eukaryotic cells. De Smedt, S. C., Demeester J., Hennink W. E., 2000. Cationic polymer based gene delivery systems. Pharmaceutical Research, Vol. 17. No. 2, 113-126.

The transfection efficiency of new cationic polymers pHPE, pHPP and pHP (0.5% aqueous solutions) was tested on a variety of cell lines using enhanced green fluorescent protein (eGFP) expressing vector. The transfection efficiency of cationic polymers was evaluated by FACS (fluorescence activated cell sorter) using three criteria, the percent of green fluorescent protein (GFP) positive cells (transfection efficiency), the percent of dead cells (toxicity) and mean fluorescence intensity (MFI).

Standart DNA Transfection Protocol into Cos7 Cells Using Hydroxyalkyleneimine Polymers as Gene Carriers Transfection of Cos-7 (SV40 transformed African green monkey kidney cell line) with eGFP expressing vector using pHPE, pHPP, pHP polymers was carried out as follows: one day before the transfection experiment, the cells were plated in a 24-well tissue culture plate at the density of 5×10$^4$ cells per well in the total volume of 1 ml DMEM culture medium supplemented with 10% FBS. The cells were incubated at 37° C. in a CO$_2$ incubator until they reached 70-80% confluency (usually within 24 h). DNA (1 μg) was diluted in 100 μl of 0.15M NaCl solution. Cationic polymers (specific amounts indicated in the FIG. 1) were deposited on the wall of the same Eppendorf tube containing DNA and vortexed immediately for 10 seconds to ensure even distribution of the material. The complexes were allowed to form for 15-20 min at room temperature and added to the cell culture in a drop-wise manner. The transfection efficiency was tested 48-72 h later by FACS.

The results show that all three hydroxyalkyleneimine polymers act as DNA carriers with Cos-7 cells (FIG. 1). In all cases the transfection efficiency at optimal polymer concentration was close to 100% and the toxicity was low.

Figure 2:
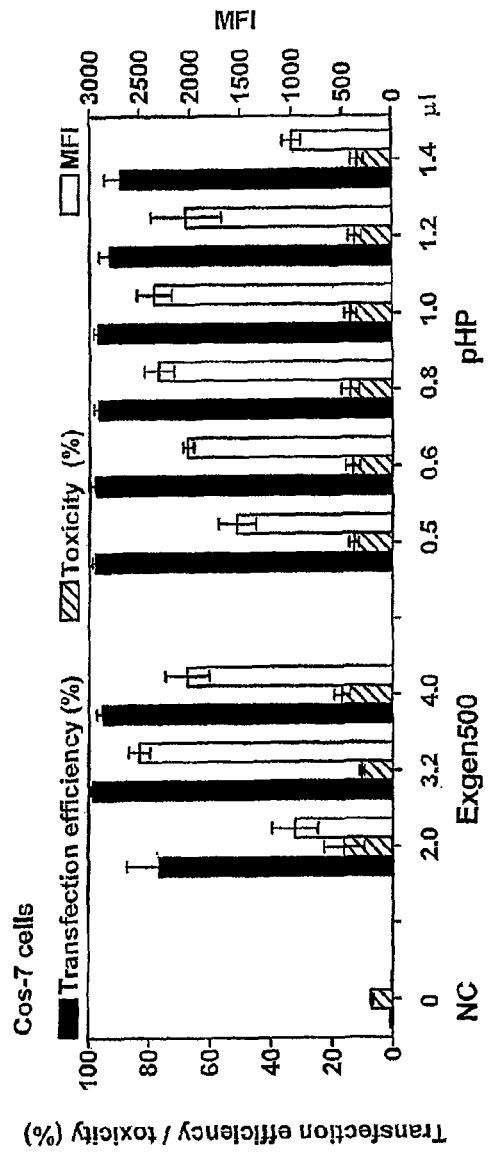
FIG. 2 shows comparison of transfection efficiency between Exgen500 and pHP using Cos-7 cells.

Considering the fact, that pHP induced the highest fluorescence, it was further tested against the ExGen500, one of the most efficient transfection reagents in the market (FIG. 2). The results indicate that using 0.5-1.4 μl of pHP per transfection, the amount of GFP$^+$ cells stays within 80-95%, the toxicity is similar to non transfected negative control, and very clear changes are observed only in fluorescence intensity. The MFI steadily increased and the highest value is registered using 1.0 μl of pHP polymer. Later the MFI value goes down following the titration of pHP. Comparing transfection values for EnGen500 and pHP, all three parameters, transfection efficiency, toxicity and MFI are nearly identical.

Comparison of Gene Delivery Agent pHP with Exgen500 Using Different Cell Lines

For the better evaluation of hydroxyalkyleneimine polymers, pHP was compared with ExGen500 by testing its effect on different cell lines.

Figure 3:
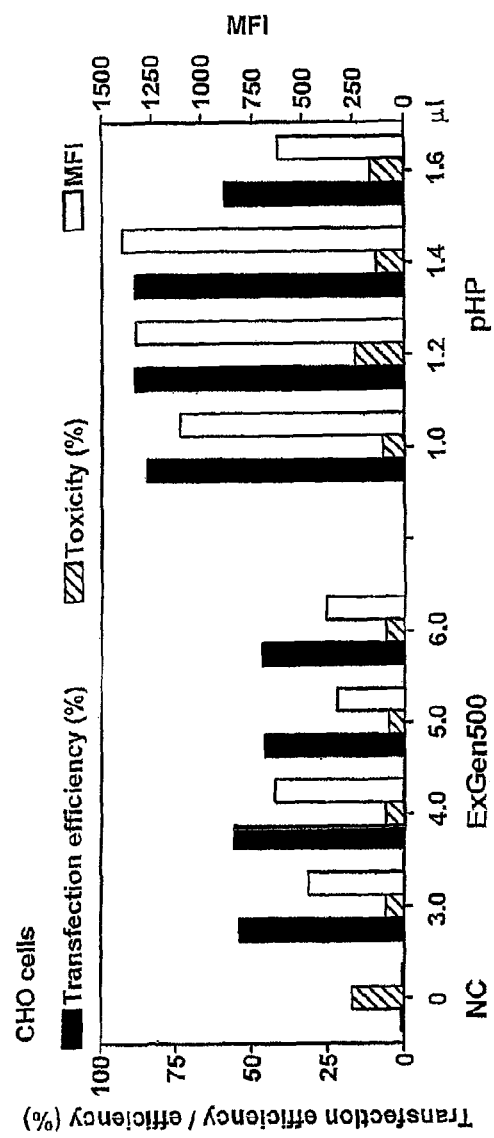
FIG. 3 shows comparison of transfection efficiency between Exgen500 and pHP using CHO cells.
Figure 4:
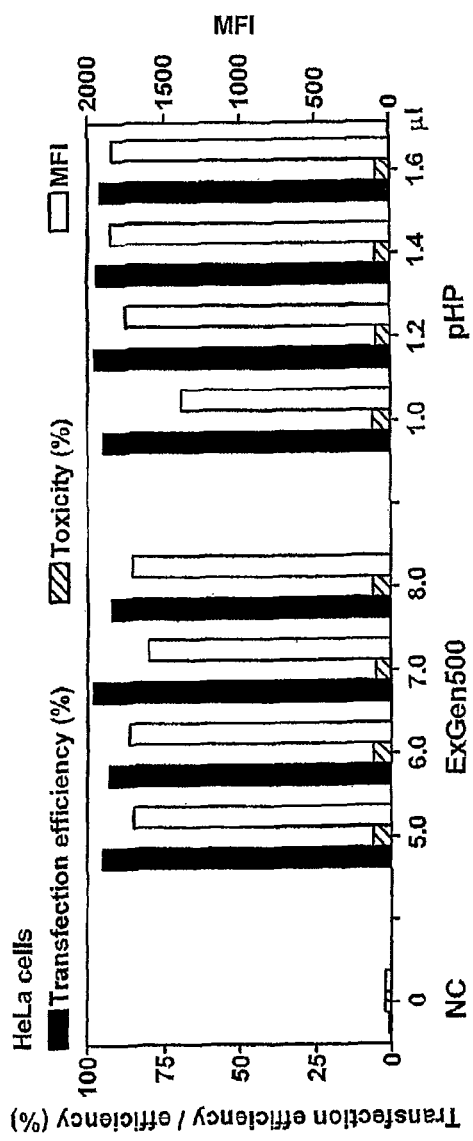
FIG. 4 shows comparison of transfection efficiency between Exgen500 and pHP using HeLa cells.
Figure 5:
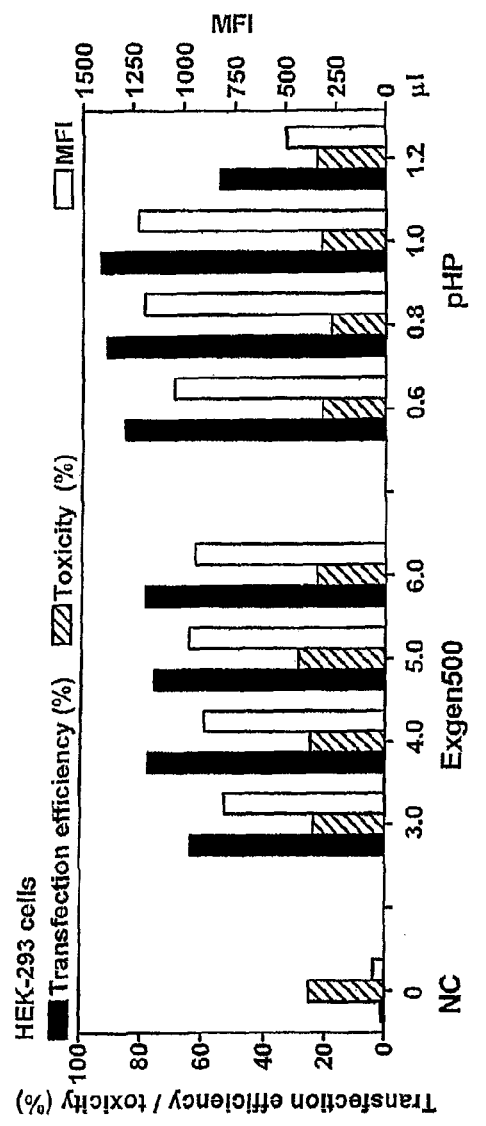
FIG. 5 shows comparison of transfection efficiency between Exgen500 and pHP using Hek-293 cells.
Figure 6:
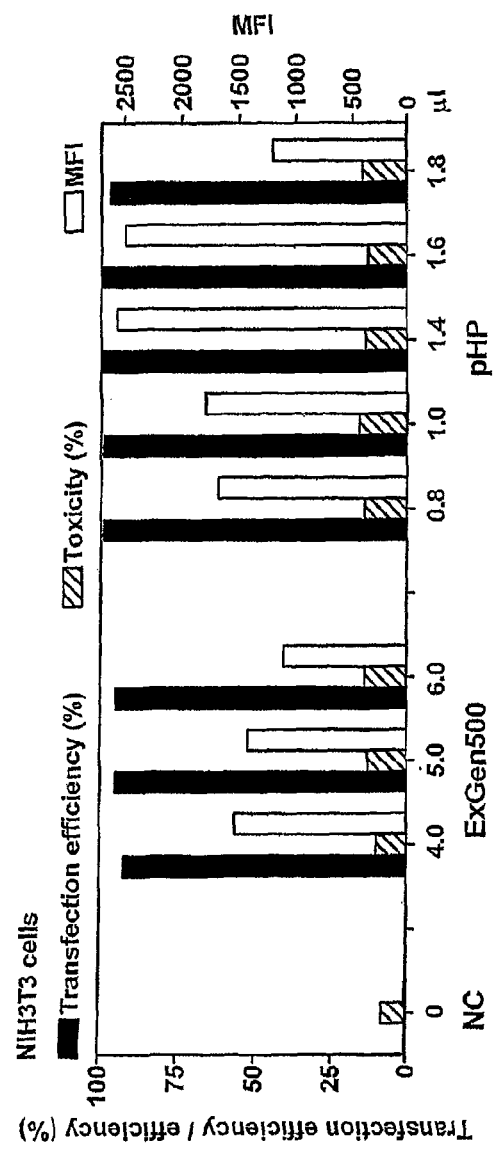
FIG. 6 shows comparison of transfection efficiency between Exgen500 and pHP using NIH3T3 cells.
Figure 7:
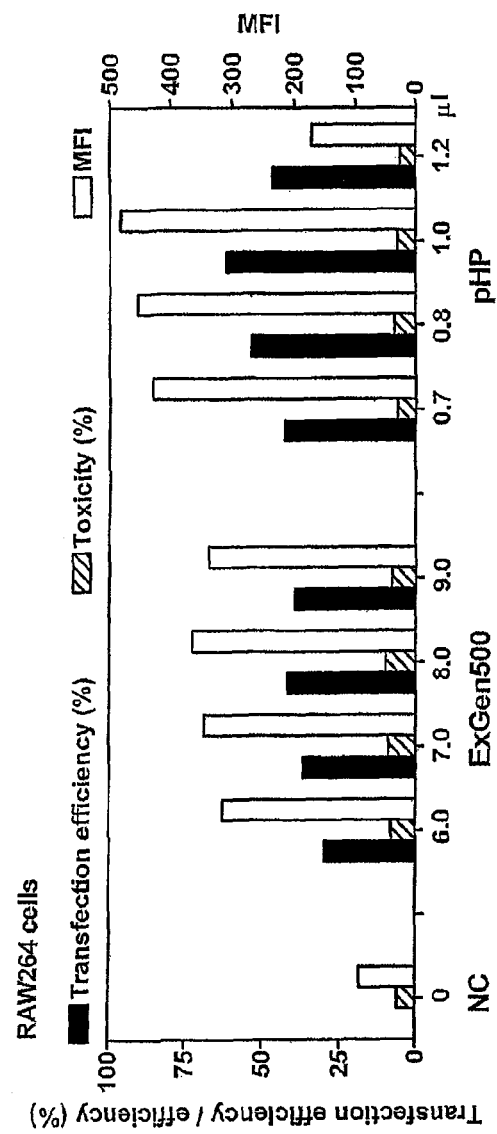
FIG. 7 shows comparison of transfection efficiency between Exgen500 and pHP using RAW264 cells.
Figure 8:
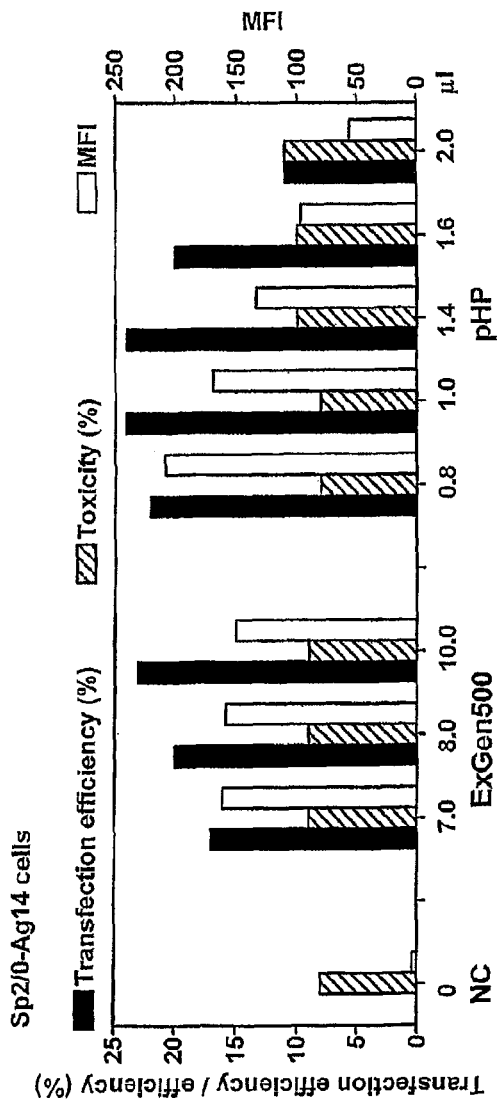
FIG. 8 shows comparison of transfection efficiency between Exgen500 and pHP using Sp2/0-Ag14 suspension cells.
Figure 9:
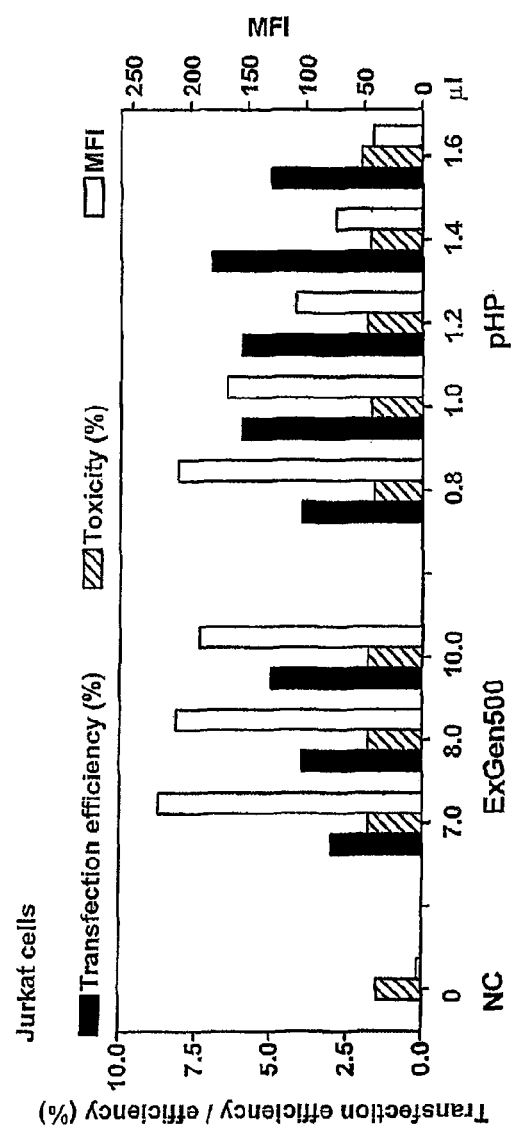
FIG. 9 shows comparison of transfection efficiency between Exgen500 and pHP using Jurkat suspension cells.

Gene transfer efficiency was tested using adherent CHO (Chinese hamster ovary-derived cell line) (FIG. 3), HeLa (Human cervical carcinoma-derived cell line) (FIG. 4), HEK293 (human embryonic kidney-derived cell line) (FIG. 5), NIH3T3 (mouse embryo fibroblast-derived cell line) (FIG. 6), semiadherent RAW264 (mouse leukaemic monocyte-macrophage derived cell line) (FIG. 7), and suspension cell lines Jurkat (Human T cell leukemia cell line) (FIG. 9) as well as Sp2/0-Ag14 (mouse myeloma) (FIG. 8).

ExGen500-DNA polyplexes were prepared in the same way as pHP starting with 3.0 µl of ExGen500 to 100 µl of DNA-0.15M NaCl solution as suggested by supplier. The results show that pHP acts similarly or better than ExGen500 on all cell types tested. The transfection efficiency in HeLa and HEK293 cell lines with both reagents reaches 90-100% with the highest MFI (slightly higher for pHP) achieved using 3 µl of ExGen500 and 1.4 µl of pHP. The toxicity remains low and comparable to what is observed with non transfected cells as a natural cell death event. In tested CHO, NIH3T3 and RAW cells the transfection efficiency is visibly better with pHP reagent. The percent of GFP$^+$ cells is 90%, 80% and 100% with CHO, RAW and NIH3T3 cells, respectively. The ExGen500 can yield only 48% and 56% GFP$^+$ cells with RAW and CHO cell lines, and up to 90% with NIH3T3 cells. The MFI is a parameter that evidently sets up pHP apart from ExGen500, the MFI is two times higher in NIH3T3, CHO and RAW cells when they are transfected using pHP as opposed to ExGen500. The toxicity in the latter cell lines was determined to remain within the normal range (5-15%) as compared to non transfected cells. Transfection of cell lines growing in suspension is problematic with any transfection reagent currently available. pHP and ExGen500 yielded only 5-7% GFP$^+$ Jurkat cells (MFI up to 200) and 24% Sp2/0-Ag14 cells (MFI 150-200). The toxicity in both cases remains the same as in non transfected cells.

Comparison of pHP Gene Delivery Efficiency with Commercially Available Transfection Reagents Using Hela Cell Line The cationic polymer pHP was further examined by comparing it with the commercially available transfection reagents that are widely used for different scientific applications.

Figure 10:
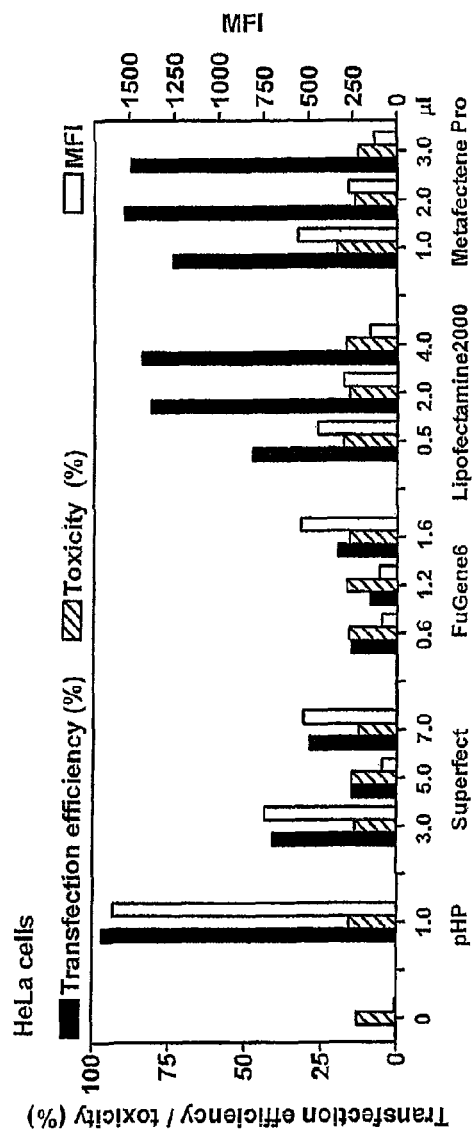
FIG. 10 shows comparison of pHP with commercial transfection transfection reagents Lipofectamine 2000, FuGENE 6, Superfect and Metafectene Pro.

PHP transfection efficiency was compared using HeLa cells with Lipofectamine 2000 (Invitrogen), FuGENE 6 (Roche), Superfect (Qiagen) and Metafectene Pro (Biontex) (FIG. 10).

The HeLa cells were seeded in 24-well tissue culture plate one day before the transfection as described above. Transfection efficiency of pHP was examined according to the protocol depicted above. DNA complexes with commercial transfection reagents Lipofectamine 2000 (Invitrogen), FuGENE 6 (Roche), Superfect (Qiagen) and Metafectene Pro (Biontex) were prepared according to the manufacturers instructions. Briefly, for Lipofectamine 2000, 0.5-5 µl of the reagent was diluted in 50 µl of serum-free DMEM, incubated for 5 min and mixed with 50 µl of prediluted DNA (0.8 µg DNA in serum-free DMEM). Upon incubation for 20 min at room temperature, the DNA-lipofectamine complexes were added to the cell culture in a drop-wise manner. For Superfect, the DNA (1 µg) was diluted in 60 µl of serum-free DMEM. The Superfect reagent (2-10 µl) was added to the DNA solution, vortexed for 10 seconds and incubated for 10 min at room temperature. The complete medium was added to the mixture and everything was layered onto the PBS-washed HeLa cells. The cells were further incubated for 3 h in a $CO_2$ incubator at 37° C., then washed with PBS and loaded with fresh cell growth supporting medium. For FuGENE 6, the reagent (0.6-1.6 µl) was diluted in 20 µl of serum-free medium and incubated for 5 min. The DNA (0.4 µg) was added to each tube, vortexed for 1 second and the mixture was incubated for 15 min at room temperature. After that it was added to the cell culture in a drop-wise manner. For MetafectenePro, the reagent (1-6 µl) was diluted in 50 µl of serum-free DMEM. The DNA (0.5 µg) was diluted in 50 µl of serum-free DMEM) and layered onto diluted MetafectenePro solution without mixing. The complexes were allowed to form for 20 min at room temperature and added drop-wise to the cell culture.

The results indicate that pHP activity is superior to any other transfection reagent. pHP performs significantly better than Superfect and FuGENE 6. Superfect yields at the best 41% GFP$^+$ HeLa cells with MFI at 740, while FuGENE gives only 20% GFP$^+$ cells with MFI at 547. These results fail in comparison to pHP with 97% GFP$^+$ cells and MFI 1600. Lipofectamine 200 and MetafectenePro come close to pHP as far as the percent of GFP expressing cells, which is 84% and 90%, respectively. However, the MFI values are clearly higher for pHP, 1600 versus 500 for both Lipofectamine2000 and MetafectenePro. ExGen500 reagent performed best out of all commercial reagents tested, however not as efficiently as pHP. The cell viability for all reagents tested was similar to non transfected control. However, Lipofectamine 2000 and MetafectenePro transfected cells showed marked increase in cellular autofluorescence levels which is an indicative of toxic side effect on an overall cell health.

Figure 11:
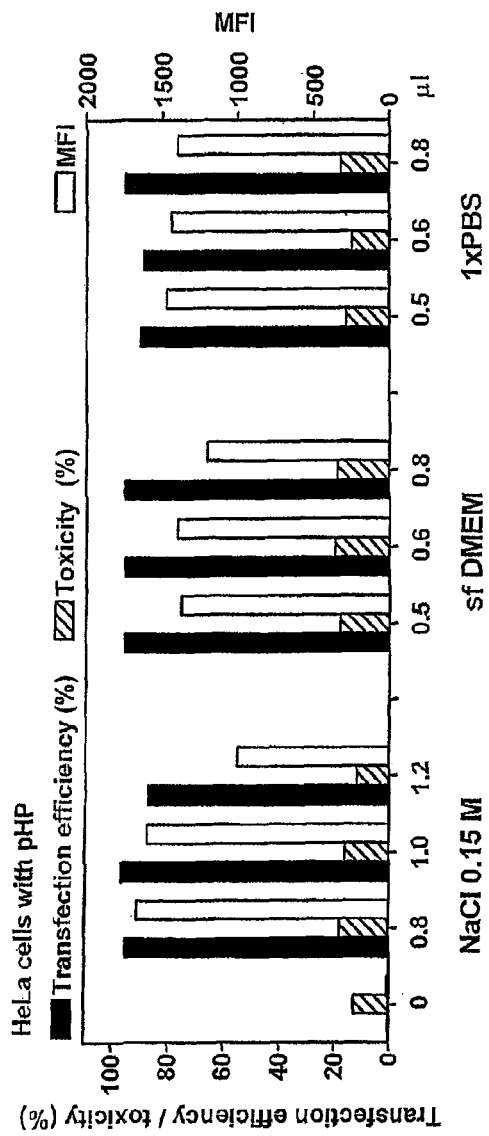
FIG. 11 shows transfection efficiency of pHP with HeLa cells using different solutions for complex formations.

Assessment of pHP Gene Delivery Efficiency Using Different Conditions for pHP-DNA Complex Formation Evaluation of pHP-DNA complex formation under different conditions and its influence on the transfection efficiency was carried out in order to determine the best possible way to compact DNA into small particles and to ensure the most efficient cargo transport through the cellular membrane. The cationic polymer pHP and DNA complexes were formed using either 0.15 M NaCl or serum-free DMEM or 1×PBS as a solvent following the basic protocol described earlier. The results indicate that there was essentially no difference in transfection efficiency irrespective of the solution used for the complex formation (FIG. 11).

Analysis of pHP as an In Vivo Transfection Agent

To expand the use of pHP beyond in vitro application, the polymer was tested in an in vivo setting by delivering pHP-DNA complexes into an animal via intravenous or intraperitoneal route and analyzing GFP expression in different tissues 48 h later. The DNA (50 or 100 ug) was diluted in 200 or 500 ul of 5% sterile glucose solution for IV or IP application, respectively. The 10-fold concentrated pHP (10 ul for IV and 20 ul for IP) was deposited on the wall of the eppendorf tube, vortexed immediately for 10 seconds and incubated for 15 minutes at room temperature. The complexes were injected into the tail vein using the 29 G needle or delivered directly into the peritoneal cavity using the 26 G needle. The animals were sacrificed 48 h later and the cell suspensions prepared from different organs (lymph nodes, spleen, kidney, liver or lungs as well as peritoneal exudate) were analyzed using the fluorescent imaging microscope Olympus.

Figure 12:
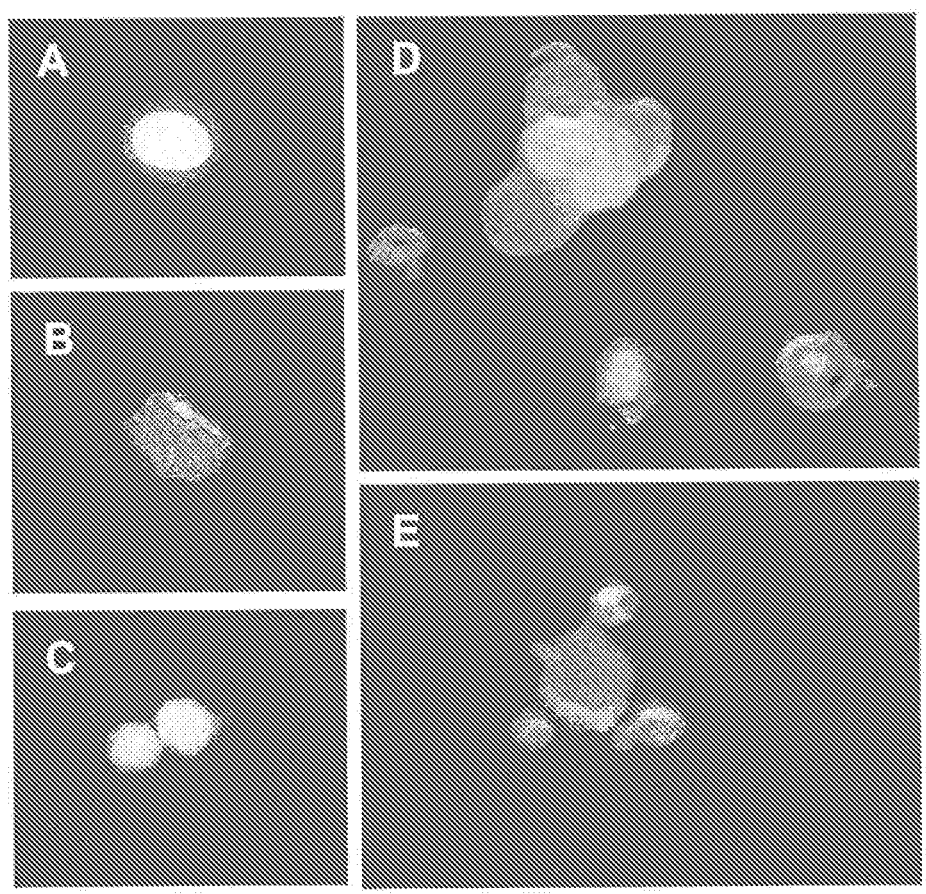
FIG. 12 shows transfection efficiency of pHP in vivo.

The results revealed GFP positive cells in the cellular preparation of every organ analyzed (FIG. 12 shows fluorescent cell images, where A, B, C, D, E represents kidney, spleen, liver, lymph node and peritoneal lavage cells, respectively). The results demonstrate that pHP enables DNA delivery into the cells in vivo, whereas no fluorescent cells were observed when GFP encoding DNA was transferred alone. The injection of pHP alone did not yield any nonspecific autofluorescence as well.

The invention claimed is:

1. A composition comprising
   (i) a modified cationic polyalkyleneimine polymer and
   (ii) at least one nucleic acid,
where the modified cationic polyalkyleneimine polymer has a repeat unit selected from

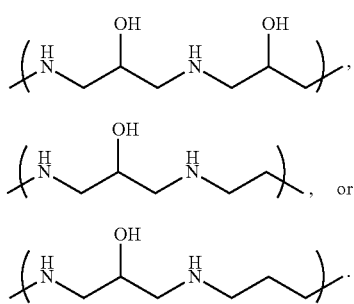

2. An agent suitable for delivering at least one nucleic acid to a cell, said agent comprising a composition as defined in claim 1 and a pharmaceutically acceptable vehicle.

3. The composition according to claim 1, wherein the modified cationic polyalkyleneimine polymer is a homopolymer.

4. The composition according to claim 1, wherein the modified cationic polyalkyleneimine polymer is a copolymer.

5. The composition according to claim 1, wherein the composition further comprises one or more adjuvants.

6. The composition according to claim 1, wherein the at least one nucleic acid is a DNA.

7. A method of delivering at least one nucleic acid to a cell comprising a step of contacting the composition of claim 1 with the cell, whereby the at least one nucleic acid is delivered to, and taken into, the cell, and where the cell is a eukaryotic cell.

8. The method according to claim 7, wherein said method is carried out in vivo.

9. The method according to claim 7, wherein said method is carried out in vitro.

10. The method according to claim 9, wherein the cell is comprised in a cultured cell line.

11. A method of making a composition as defined in claim 1, comprising the steps of:
    (a) providing a solution containing the at least one nucleic acid; and
    (b) mixing the solution with the modified cationic polyalkyleneimine polymer, resulting in the composition of claim 1.

12. The method according to claim 11, further comprising conducting a polycondensation reaction between first monomers, each having two reactive groups, and second monomers, each having two reactive groups, to provide the modified cationic polyalkyleneimine polymer, wherein each of said reactive groups are selected from group consisting of —Cl, —Br, —I, tosyl, mesyl, —NH$_2$ and NHR.

13. The method according to claim 12, wherein the two reactive groups of the second monomers are both Br.

14. An agent suitable for delivering at least one nucleic acid to a cell comprising a composition comprising poly(2-hydroxypropyleneimine) and at least one nucleic acid.

15. A composition comprising (i) poly(2-hydroxypropyleneimine ethyleneimine) or poly(2-hydroxypropyleneimine propyleneimine) and (ii) at least one nucleic acid.

16. A composition comprising poly(2-hydroxypropyleneimine) and at least one nucleic acid.

* * * * *